United States Patent [19]
Kojima et al.

[11] Patent Number: 5,801,023
[45] Date of Patent: Sep. 1, 1998

[54] ANTIPARASITIC PYRROLOBENZOXAZINE COMPOUNDS

[75] Inventors: Yasuhiro Kojima, Nishio; Yuji Yamauchi, Handa; Nakao Kojima, Nagoya, all of Japan; Bernard F. Bishop, Nr. Sandwich, England

[73] Assignee: Pfizer Inc., New York, N.Y.

[21] Appl. No.: 669,555

[22] PCT Filed: Jan. 11, 1995

[86] PCT No.: PCT/JP95/00025

§ 371 Date: Nov. 29, 1996

§ 102(e) Date: Nov. 29, 1996

[87] PCT Pub. No.: WO95/19363

PCT Pub. Date: Jul. 20, 1995

[30] Foreign Application Priority Data

Jan. 14, 1994  [JP]  Japan ..................... 6-15825

[51] Int. Cl.$^6$ .............. C12P 17/00; C12P 17/16; A61K 31/33; A61K 31/535
[52] U.S. Cl. .............. 435/117; 435/118; 435/119; 435/120; 435/121; 435/127; 435/128; 435/132; 435/135; 435/147; 435/155; 435/156; 435/171; 514/183; 514/728.8; 514/229.5; 514/230.5; 514/729.8; 514/359; 514/408; 514/410; 514/411; 514/412; 514/461; 514/510; 544/1; 544/63
[58] Field of Search .............. 514/422, 183, 514/228.8, 229.5, 230.5, 229.8, 359, 408, 410, 411, 412, 461, 510, 513, 743; 548/429; 549/359; 435/117, 118, 119, 120, 121, 127, 128, 132, 135, 147, 155, 156, 171

[56] References Cited

U.S. PATENT DOCUMENTS 5,073,567  12/1991  Kojima et al. .............. 514/450

FOREIGN PATENT DOCUMENTS 2 240 100  7/1991  United Kingdom.

OTHER PUBLICATIONS

Paden, J.W. (1968) Mycopathol. Mycol. Appl. 36: 161–164, 1968.

*Primary Examiner*—Stephen Walsh
*Assistant Examiner*—Michael Pak
*Attorney, Agent, or Firm*—Peter C. Richardson; Gregg C. Benson; Carl J. Goddard

[57] ABSTRACT

This invention provides compounds of the following chemical formula or their pharmaceutically-acceptable salts:

wherein R is hydrogen or chloro. Also, the present invention provides a process for the production of the compound of formula I, which comprises cultivating a microorganism having the identifying characteristics of *Aspergillus fischeri* var. *thermomutatis* ATCC 18618 or the like, and then isolating the compound of formula I from the fermentation broth. The pyrrolobenzoxazine compounds of formula I of this invention have broad antiparasitic activity, and thus are useful as antiparasitic agents, especially as anthelmintics.

9 Claims, No Drawings

ANTIPARASITIC PYRROLOBENZOXAZINE COMPOUNDS

TECHNICAL FIELD

The present invention relates to novel pyrrolobenzoxazine compounds, a process for their production and their use. More particularly, the present invention relates to a process for production of novel pyrrolobenzoxazine compounds by cultivating *Aspergillus fischeri* var. *thermomutatis* ATCC 18618. Further, the present invention relates to an antiparasitic agent which comprises a pyrrolobenzoxazine compound of this invention as an effective ingredient.

BACKGROUND ART

It is known that the pyrrolobenzoxazine UK-88,051 is a broad spectrum antiparasitic agent possessing anthelmintic, ectoparasiticidal, insecticidal activity with application in the areas of animal and human health, agriculture and horticulture (United Kingdom Patent No. 2240100). This compound is produced by fermentation of a fungal microorganism Chrysosporium sp. ATCC 20975. In this field, the investigation on novel compounds having excellent activity has been continuously carried out.

An objective of the present invention is to provide novel compounds with excellent activity against insect pests, acari, helminths (e.g., free living nematodes) and endo- and ectoparasites afflicting animals. Also, another objective of the present invention is to provide a process for producing such compounds, and a pharmaceutical composition comprising the same.

BRIEF DESCRIPTION OF THE INVENTION

Accordingly, the present invention provides novel pyrrolobenzoxazine compounds of the following planar chemical formula or their pharmaceutically-acceptable salts:

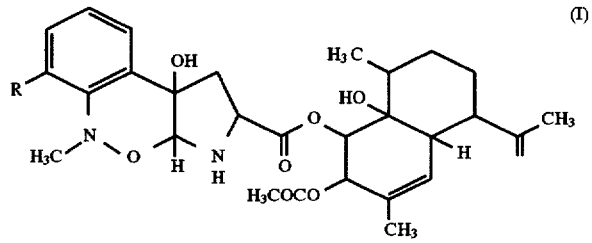

(I)

wherein R is hydrogen or chloro. It is believed that these compounds have the following absolute chemical formula:

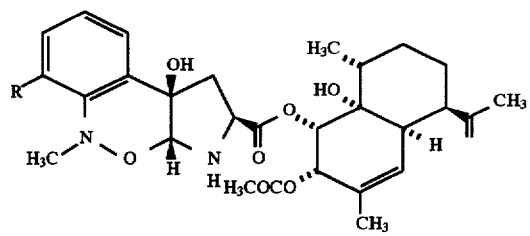

(A)

wherein R is hydrogen or chloro.

Also, the present invention provides a process for the production of the compound of formula I, which comprises fermenting a microorganism having the identifying characteristics of *Aspergillus fischeri* var. *thermomutatus* ATCC 18618, or a mutant, genetically-transformed or recombinant form thereof, having the ability to produce the compound of formula I, and then isolating the compound of formula I from the fermentation broth.

The pyrrolobenzoxazine compounds of formula I of this invention have broad antiparasitic activity, and thus are useful as antiparasitic agents, especially as ectoparaciticides. Accordingly, the present invention also provides a pharmaceutical composition for the treatment or prevention of parasitic infection in mammalian subject which comprises a therapeutically-effective amount of the compound of formula I together with a pharmaceutically-acceptable carrier; and a method for the treatment or prevention of a parasitic infection in non-human mammalian subject, which comprises administering to said subject a therapeutically-effective amount of the compound of formula I.

DETAILED DESCRIPTION OF THE INVENTION

The culture which produces the compounds of the present invention, *Aspergillus fischeri* var. *thermomutatus* ATCC 18618, was obtained from the American Type Culture Collection (ATCC located in 12301 Parklawn Drive, Rockville, Md. 20852, USA). The taxonomical properties of *A. fischeri* var. *thermomutatus* ATCC 18618 are reported in the literature (Mycopathol. Mycol. Appl., 36, 161–164, 1968). The culture has been deposited further at Agency of Industrial Science and Technology located in 1-3, Higashi 1-chome Tsukuba-shi, Ibaraki-ken, Japan on Dec. 15, 1993, under Accession No. FERM BP-4497.

In addition, mutant strains of *Aspergillus fischeri* var. *thermomutatus* ATCC 18618, can be used. Such mutant strains can be obtained spontaneously, or by the application of known techniques, such as exposure to ionising radiation, ultraviolet light, and/or chemical mutagens such as N-methyl-N-nitrosourethane, N-methyl-N'-nitro-N-nitrosoguanidine, ethyl methyl sulphate, etc. Genetically transformed and recombinant forms include mutants and genetic variants produced by genetic engineering techniques, including for example recombination, transformation, transduction, protoplast fusion, etc. The invention also extends to pyrrolobenzoxazine compounds produced by said process.

Fermentation of the culture ATCC 18618 can be carried out using standard procedures, well-known in the art for fungi of the genus Aspergillus. For example, fermentation may take place on suitable solid media under aerobic conditions at a temperature in the range of 20° to 45° C. for 3 to 30 days, preferably at 24° to 37° C. for 7 to 21 days. Alternatively, fermentation may take place in aqueous nutrient media containing suitable sources of carbon, nitrogen and trace elements such as iron, cobalt, copper and zinc for a period of several days under aerobic conditions at a temperature in the range at 20° to 45° C. for 2 to 21 days, preferably at 24° to 37° C. for 3 to 10 days.

The novel pyrrolobenzoxazine compounds of the present invention, 2-acetoxy-1,2,4a,5,6,7,8,8a-octahydro-8a-hydroxy-3,8-dimethyl-5-(1-methylethenyl)-1 -naphthalenyl 6-chloro-1,2,3,3a,5,9b-hexahydro-9b-hydroxy-5-methylpyrrolo[2,3-c][2,1]benzoxazine-2-carboxylate (CJ-12,662) and 2-acetoxy- 1,2,4a,5,6,7,8,8a-octahydro-8a-hydroxy-3,8-dimethyl-5-(1-methylethenyl)- 1-naphthalenyl, 1,2,3,3a,5,9b-hexahydro-9b-hydroxy-5-methylpyrrolo[2,3-c][2,1]benzoxazine-2-carboxylate (CJ-12,663), which are shown in the following scheme, are obtained from fermentation of the culture ATCC 18618, and can be separated by conventional extractions and various techniques of chromatography.

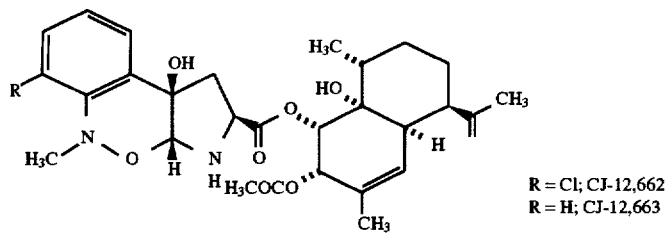

R = Cl; CJ-12,662
R = H; CJ-12,663

Though the novel pyrrolobenzoxazine compounds of this invention are slightly soluble in water, they are easily soluble in organic solvents. Thus, the novel pyrrolobenzoxazine compounds can be recovered from the fermentation broth by solvent extraction. For example, the whole fermentation broth is partitioned between water and an organic solvent such as chloroform, ethyl acetate or methyl isobutyl ketone. The extract is dried over drying agent and concentrated. The residue dissolved in adequate solvent is chromatographed to separate the pyrrolobenzoxazine compounds by eluting with a solvent (a single solvent or mixture of the solvents with various ratios, such as hexane: EtOAc=1 : 1). Many kinds of powder solids such as silica gel, reverse phase silica gel or dextran can be used as supports or stationary phases. High performance liquid chromatography (HPLC) and thin layer chromatography (TLC) are advantageous for separating the pyrrolobenzoxazine compounds. The existence of the pyrrolobenzoxazine compounds can be confirmed by measuring the antiparasitic activity for each fraction of the chromatography.

The acid addition salts of a compound of formula I of this invention are prepared by treating carefully the present compound with a substantially equivalent amount of the chosen mineral or organic acid in an aqueous solvent or in a suitable organic solvent. Upon careful evaporation of the solvent, the desired solid salt is readily obtained. The acids which are used to prepare the pharmaceutically-acceptable acid addition salts of the aforementioned pyrrolobenzoxazine base compounds of this invention are those which form non-toxic acid addition salts, i.e., salts containing pharmaceutically-acceptable anions such as hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate. The antiparasitic activity of the compounds of formula I against the larval stage of the blowfly Lucilia cuprina is measured by using a standard procedure (e.g., Techniques for testing Insecticides. Ed. J. R. Busvine Publ. Commonwealth Institute for Entomology London, 1957) in which first instar larvae are kept in contact with filter paper treated with a test compound. The test compound is first applied to the paper as an acetone solution. The treated filter papers are then placed in tubes containing foetal calf serum and the first instars are added. CJ-12,662 killed 100% of the larvae when applied to the filter paper at a level of 40 mg/m$^2$.

The pyrrolobenzoxazine compounds of formula I of this invention are useful as antiparasitic agents in a variety of mammalian species including man.

They can be used for the prevention or treatment of systemic infections caused by endoparasites including, in particular, helminthiasis which is most frequently caused by a group of parasitic worms described as nematodes and which can cause severe economic losses in mammals such as swine, sheep, horses and cattle as well as affecting domestic animals and poultry. They are also of value in treating ectoparasite infections including in particular arthropod ectoparasites of animals and birds such as ticks, mites, lice fleas, blowfly, biting insects and migrating dipetrous larvae which affect cattle and horses. They are also insecticides, active against household pests such as the cockroach, clothes moth, carpet beetle and the housefly as well as being useful against insect pests of stored grain and of agricultural plants such as spider mites, aphids, caterpillars and against migratory orthopterans such as locusts.

For these purposes, they can be administered to a mammalian subject orally or parenterally.

As an alternative, the compounds of formula I may be administered with the animal feedstuff and for this purpose a concentrated feed additive or premix may be prepared for mixing with the normal animal feed.

The novel pyrrolobenzoxazine compounds of the present invention may be administered alone or in combination with pharmaceutically-acceptable carriers or diluents, and such administration can be carried out in single or multiple doses. Particularly, the novel therapeutic agents of the invention can be administered in a wide variety of different dosage forms, i.e., they may be combined with various pharmaceutically-acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups and the like. For use as an insecticide and for treating agricultural pests, sprays, dusts, pour-on formulations, emulsions and the like are preferable in accordance with standard veterinary practice. Such carriers include solid diluents or fillers, sterile aqueous media, various non-toxic organic solvents, etc. Moreover, oral pharmaceutical compositions can be suitably sweetened and/or flavored. In general, the therapeutically-effective compounds of this invention are present in such dosage forms at concentration levels ranging about 5 to 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, the addition of lubricating agents such as magnesium stearate, sodium lauryl sulfate and talc is often very useful for tabletting purposes. Solid compositions of a similar type may also be employed as fillers in gelatine capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of the pyrrolobenzoxazine compounds of the present invention in either sesame or peanut oil or in aqueous propylene glycol may be employed. The aqueous solutions should be suitably buffered (preferably pH>8) if necessary, and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art.

Additionally, it is also possible to administer the compounds of the present invention topically to an affected part such as the skin and this may preferably be done by way of creams, jellies, gels, pastes, ointments, pour-ons, sprays and the like, in accordance with standard pharmaceutical practice.

The formulations will vary with regard to the weight of active compound, depending on the species of host mammalian to be treated, and depending on the severity and type of infection and the body weight of the host. Generally a dosage level that is in the range of from about 1 to 100 mg per kg of body weight per day is desirably employed. Nevertheless, when administering to the animals, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

EXAMPLES

The present invention is illustrated by the following example. However, it should be understood that the invention is not limited to the specific details of this example. UV spectra were recorded using a Hewlett Packard 1090M diode-array spectrophotometer. All NMR spectra were measured in $CDCl_3$ by a Varian Unity 500 MHz spectrometer unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad. Mass spectra (LSIMS) were measured by a Kratos Concept 1S mass spectrometer. Thermospray mass spectrometry was performed using a VG-Trio-1000 quadrupole mass spectrometer. Samples were introduced from methanolic solution directly on the probe.

Example 1

The culture *Aspergillus fischeri* var. *thermomutatus* ATCC 18618 was inoculated on a slant of ATCC Medium 325 consisting of malt extract 20 g, glucose 20 g, peptone 1 g, agar 20 g and distilled water 1 l, and incubated at 26° C. for 2 weeks. Spore suspension of the mature slant culture was used to inoculate a solid production medium in a 1—1 Erlenmyer flask. The solid production medium in the flask consisted of glucose 0.5 g, glycerol 1.5 g, peptone 0.25 g, NaCl 0.1 g, bran 20 g and tap water 50 ml. Thirty solid production flasks were incubated under stationary conditions at 26° C. for 2 weeks. Two hundred ml of acetone was added to each of the 30 1—1 flasks; contents of these flasks were then combined, stirred and filtered. After removal of the solvent, the residue was extracted with 2 l of ethyl acetate. The extract was dried over anhydrous $Na_2SO_4$ and evaporated. The resultant oily residue (3 g) was loaded on a silica gel column (Merck Kieselgel 60, 70–230 mesh) and eluted with n-hexane : ethyl acetate (1 : 1). Then further purification was carried out on a Sephadex LH-20 column (3.0×90 cm, MeOH). Fractions with antiparasitic activity were combined and concentrated. The active fraction was applied to preparative HPLC (YMC-Pack ODS-AM column 5 µ, methanol : $H_2O$=4 : 1) to obtain pure CJ-12,662 (129 mg) and CJ-12,663 (27 mg).

Physico-chemical properties of CJ-12,662

Formula: $C_{29}H_{37}N_2O_7Cl$

LSIMS m/z=561.239 $(M+H)^+$ (Calcd.: 561.245 for $C_{29}H_{37}N_2O_7Cl$) UV λ nm: 217, 248, 287

$^1H$ NMR ($CDCl_3$): 7.4 (1H, d), 7.25 (1H, d), 7.05 (1H, t), 5.5 (1H, bs), 5.4 (1H, bs), 5.2 (2H, m), 5.05 (1H, bs), 4.8 (1H, bs), 4.15 (1H, m), 3.65 (1H, bs), 3.35 (3H, s), 3.1 (1H, s), 2.75 (1H, m), 2.5–2.65 (3H, m), 2.35 (1H, s), 2.15 (3H, s), 2.0–2.15 (1H, m), 1.85 (3H, s), 1.65 (3H, s), 1.3–1.65 (4H, m) and 0.9 (3H, d).

$^{13}C$ NMR ($CDCl_3$): 174.9 (s), 169.9 (s), 146.5 (s), 144.1 (s), 131.6 (s), 129.9 (d), 129.6 (s), 127.3 (d), 125.7 (d), 124.4 (d), 123.5 (s), 111.5 (t), 84.5 (d), 76.1 (s), 74.3 (d), 73.4 (s), 72.7 (d), 58.2 (d), 42.1 (q), 41.2 (t), 40.9 (d), 39.2 (d), 30.6 (d), 30.1 (t), 25.8 (t), 22.4 (q), 20.7 (q), 19.7 (q) and 14.6 (q).

Physico-chemical properties of CJ-12,663

Formula: $C_{29}H_{38}N_2O_7$

Mass spectrum (thermospray) m/z=527 $(M+H)^+$ (Calcd.: 527 for $C_{29}H_{38}N_2O_7H^+$) UV λ nm: 217, 248, 287

$^1H$ NMR ($CDCl_3$): 7.45 (1H, d), 7.25 (1H, dd), 7.0 (1H, dd), 6.75 (d, 1H), 5.5 (1H, bs), 5.4 (1H, bs), 5.2 (2H, m), 5.05 (1H, bs), 4.8 (1H, bs), 4.15 (1H, d), 4.0 (1H, m), 3.2 (3H, s), 2.45–2.9 (6H, m), 2.25 (3H, s), 1.9–2.2 (1H, m), 1.9 (3H, s), 1.7 (3H, s), 1.3–1.65 (4H, m) and 0.9 (3H, d).

We claim:

1. A substantially pure compound of formula (I) or its pharmaceutically-acceptable salts:

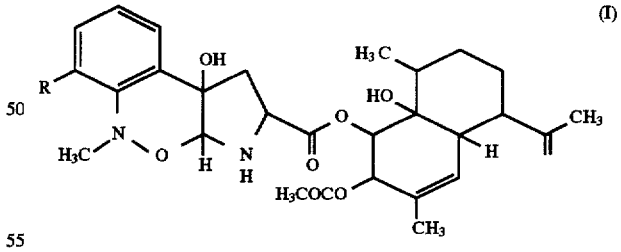

(I)

wherein R is hydrogen or chloro.

2. A compound according to claim 1, wherein R is hydrogen.

3. A compound according to claim 1, wherein R is chloro.

4. A process for the production of a compound according to claim 1, which comprises cultivating a microorganism having the identifying characteristics of *Aspergillus fischeri* var. *thermomutatus* ATCC 18618, or a mutant, genetically-transformed or recombinant form thereof, having the ability to produce a compound according to claim 1, and then isolating a compound of claim 1 from the fermentation broth.

5. A process according to claim 4, wherein the cultivation is carried out under aerobic conditions on a nutrient solid medium or in a nutrient aqueous medium containing assimilable sources of carbon, nitrogen and minerals, until a significant amount of a compound of claim 1 accumulates.

6. A process according to claim 5, wherein the microorganism is *Aspergillus fischeri* var. *thermomutatus* ATCC 18618.

7. A pharmaceutical composition for the treatment or prevention of parasitic infection in mammalian subject, which comprises a therapeutically-effective amount of a compound according to claim 1 together with a pharmaceutically-acceptable carrier.

8. A pharmaceutical composition according to claim 7 in the form of an oral, injectable or pour-on formulation, or in the form of a spray or dust, or in the form of a concentrated feed additive, premix or supplement for incorporation with the normal animal feed.

9. A method for the treatment or prevention of a parasitic infection in non-human mammalian subject, which comprises administering to said subject a therapeutically-effective amount of a compound according to claim 1.

* * * * *